Jan. 20, 1970 T. HEGG Plant Pat. 2,962
POINSETTIA PLANT
Filed May 28, 1968
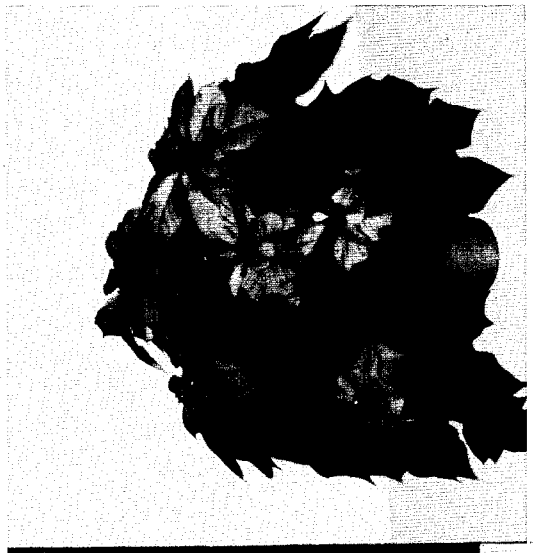
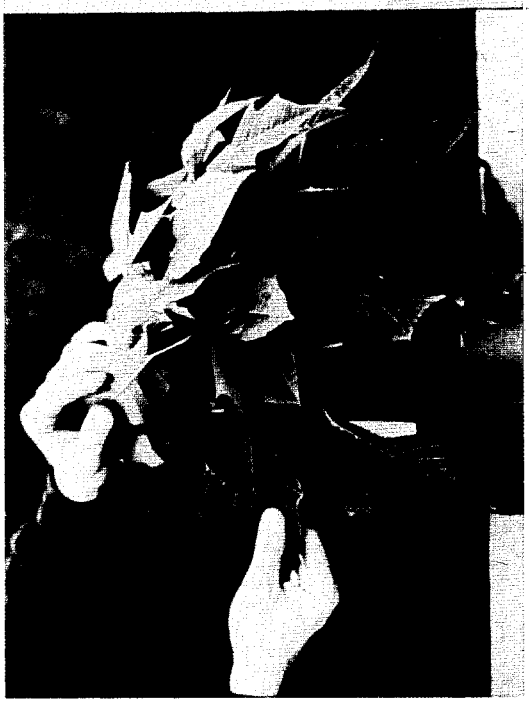
Inventor.
Thormod Hegg
By: Robb & Robb
Attorneys.

United States Patent Office

Plant Pat. 2,962
Patented Jan. 20, 1970

2,962
POINSETTIA PLANT

Thormod Hegg, Lierbyen, Norway, assignor to Paul Ecke Inc., Encinitas, Calif., a corporation of California Filed May 28, 1968, Ser. No. 732,786
Int. Cl. A01h 5/02
U.S. Cl. Plt.—86 1 Claim The present invention relates to a new and distinct variety of poinsettia plant (botanically known as *Euphorbia pulcherrima*), which was discovered by me as a sport of an unnamed poinsettia variety of unknown parentage.

At the time of my discovery aforesaid, I was growing many poinsettia seedlings of various varieties of unknown parentage, in my greenhouses at Lier, Norway, and my attention was attracted to one particular plant which stood out because of its unusual self-branching habit. Ordinarily, all other poinsettia varieties known to me will not develop side shoots and multiple blooms unless the terminal buds are pinched off. Accordingly, I recognized the self-branching habit of the new sport, without pinching, as a commercially valuable feature, and I, therefore, took steps to carefully preserve the new sport and keep it under close observation, together with asexual reproductions thereof produced by me by vegetative cuttings planted in my greenhouses at Lier, Norway. These observations fully confirm the self-branching habit of the new sport which is combined with other desirable features, representing a unique combination of charecteristics which are outstanding in the new sport and distinguish it from all other poinsettia varieties known to me, as evidenced by the following:

(1) A short-growing and compact plant habit;
(2) A uniform and fast rooting habit;
(3) A self-branching habit resulting in the production of multiple blooms without pinching off the terminal buds as required for other poinsettia varieties;
(4) Attractive green foliage and attractive red bracts, with the foliage being lighter in color than the foliage of the variety known in the United States as "Paul Mikkelsen" (U.S. Plant Patent No. 2,328), and the red bracts somewhat corresponding to the bracts of the above-mentioned patented variety, but the uppermost leaves also typically turning bright red, though they always show green veins and green leaf-edges; and
(5) Long-lasting plant qualities.

The accompanying drawing shows typical specimen plants of my new poinsettia, respectively depicting the bracts in one view and the plant habit without bracts in another view on a larger scale, as illustrated in color as nearly true as it is reasonably possible to make the same in a color illustration of this character.

The following is a detailed description of my new variety, with color terminology in accordance with Wilson's Horticultural Colour Chart, except where general color terms of ordinary significance are obvious, as based on specimens grown in Norway and also at Encinitas, Calif., U.S.A.:

Parentage: Sport of an unnamed and unpatented poinsettia variety of unknown parentage.

Propagation: Holds its distinguishing characteristics through succeeding propagations by vegetative cuttings.

Form: Short growing; compact.

Habit of growth: Self-branching; contrary to other poinsettia varieties, does not require pinching off terminal buds to produce multiple blooms; as many as ten side shoots develop without pinching, but when pinched, the side shoots become even more vigorous Rooting habit: Very uniform and very fast.

Blooming habit: The blooming is more predictable than other known varieties, and it is a "9-week" variety.

Blooming season: Blooms predictably and in time for Christmas season and well beyond through at least the month of April; is also a good variety for flowering in spring, summer and autumn.

Foliage: The shape of the leaves vary a little from other known varieties.

*Shape*:—Most typical leaves are more ovtate-acuminate, and only seldom lobed.
*Color*.—New foliage: upper side—Pod Green, Plate 061; lower side—Pod Green, Plate 061/1. Old foliage: upper side—Spinach Green, Plate 0960; lower side—Spinach Green, Plate 0960/2.

Bracts: Obovate; relatively broad; bright red color. Color: upper side—Currant Red, Plate 821/2; under side—Rhodonite Red, Plate 0022.

Flowers (cyathia): In comparison with the variety "Paul Mikkelsen," the cyathia are, when no shortday treatment is given, formed a little earlier, are more in number, and have a strong yellow pollen and are generally stronger, with the tendency to splitting being only very slight, and the cyathia do not drop off prematurely and last as long as the bracts.

Reproductive organs:

*Stamens*.—Quite numerous; from about ⅛ inch to ¾ inch long. Color—Currant Red, Plate 821/2.
*Pollen*.—Color—Canary Yellow, Plate 2.
*Styles*.—Color—Blood Red, Plate 820.
*Ovaries*.—Color—Scheele's Green, Plate 860/1.
*Nectar cups*.—Color—Lemon Yellow, Plate 4/1.

General observations: The principal feature of novelty of this new variety is the self-branching plant habit, without the need of pinching, and while other characteristics, earlier mentioned, vary also from other known varieties, their combination with the principal feature represents a new and unique combination.

I claim:

1. A new and distinct variety of poinsettia plant, substantially as herein shown and described, characterized particularly as to novelty by the unique combination of a short-growing and compact plant habit, a uniform and fast rooting habit, a self-branching habit resulting in the production of multiple blooms without pinching off the terminal buds as required for other poinsettia varieties, attractive green foliage and attractive red bracts, with the foliage being lighter in color than the foliage of the variety known in the United States as "Paul Mikkelsen" (U.S. Plant Patent No. 2,328), and the red bracts somewhat corresponding to the bracts of the above-mentioned patented variety, but the uppermost leaves also typically turning bright red, though they always show green veins and green leaf-edges, and long-lasting plant qualities.

No references cited.

ROBERT E. BAGWILL, Primary Examiner